United States Patent [19]
Farzin-Nia et al.

[11] Patent Number: 5,257,558
[45] Date of Patent: Nov. 2, 1993

[54] MEDICAL/DENTAL PLIERS

[75] Inventors: Farrokh Farzin-Nia, Inglewood, Calif.; Rohit C. L. Sachdeva, Plano, Tex.

[73] Assignee: Ormco Corporation, Glendora, Calif.

[21] Appl. No.: 978,094

[22] Filed: Nov. 17, 1992

[51] Int. Cl.⁵ .............................................. B25B 7/02
[52] U.S. Cl. ........................................ 81/418; 30/254; 433/159; 433/4
[58] Field of Search ......................... 81/416, 900, 418; 433/4, 159; 30/254

[56] References Cited

U.S. PATENT DOCUMENTS

| 2,674,800 | 4/1954 | Osborn et al. | 433/159 |
| 3,781,993 | 1/1974 | Cusato | 433/4 |
| 3,834,026 | 9/1974 | Klein | 433/159 |

Primary Examiner—James G. Smith
Attorney, Agent, or Firm—Wood, Herron & Evans

[57] ABSTRACT

Medical/dental pliers made from titanium based alloy material having jaws for gripping objects with gripping faces which are coated with a hard and wear resistant material of sufficient thickness to be structurally self-supportive when the pliers are used to grip an object which is harder than the titanium based alloy material underlying the coating. The surface of each coating has good gripping characteristics.

12 Claims, 1 Drawing Sheet

MEDICAL/DENTAL PLIERS

FIELD OF THE INVENTION

This invention relates to medical/dental pliers, and more particularly, to orthodontic pliers made from titanium based alloy materials.

BACKGROUND OF THE INVENTION

It has become more and more necessary for medical/dental instruments, such as pliers, to be disinfected and sterilized. Present methods employed for such disinfection or sterilization often cause discoloration or corrosion of the orthodontic instruments, even those made of stainless steel. Compared to stainless steel, titanium based alloys can typically last much longer in the harsh environments found in such disinfection and sterilization methods. In addition, titanium based alloys are generally lighter in weight than stainless steel. Thus, orthodontic pliers made from titanium based alloys are more corrosion resistant and generally lighter in weight than comparable pliers made of stainless steel. The improved corrosion resistance can increase the useful life of the pliers, and the lighter weight can provide better response (i.e., feel) when the pliers are manipulated, such as when used for bending wires.

Heretofore, however, titanium based alloys have been considered unsuitable for making medical/dental pliers. Medical/dental pliers, like most pliers, generally include a pair of plier halves, with each plier half having a handle, a pivot section, and a jaw with a gripping face. The two plier halves are pivotally connected at their pivot sections such that relative movement of the handles will cause the gripping surfaces to come together in a gripping fashion. One problem with pliers made from titanium based alloys is that they are likely to exhibit excessive wear, such as galling, at the pivot joint. In addition, the gripping faces of the jaws of such pliers are susceptible to being deformed or having indentations formed therein when an object harder than the titanium based alloy material, for example a stainless steel orthodontic appliance, is gripped between the jaws.

It is known to coat the gripping faces of medical/dental pliers made from titanium based alloys with a layer of titanium nitride to provide a wear resistant gripping surface on the gripping faces. However, the gripping faces of these pliers are still susceptible to being indented when used to hold hard objects. In addition, when such an indentation occurs, the titanium nitride coating is prone to crack.

SUMMARY OF THE INVENTION

In accordance with the present invention, medical/dental pliers made from titanium based alloys are provided which are less likely to have indentations formed in their gripping faces even when the pliers are used to hold an object which is harder than the titanium based alloy itself, such as a stainless steel orthodontic appliance. The present invention is also directed to medical/dental pliers made from titanium based alloys which are less likely to exhibit wear, such as galling, in the pivot joint area of the pliers.

One problem with previous pliers made from titanium based alloy materials having a hard and wear resistant titanium nitride coating on their gripping faces is the thinness of the coating. Coatings of titanium nitride are relatively thin, with a maximum thickness of only about 5 microns. The titanium based alloy material underlying the coating is much softer than the titanium nitride coating which is typically about RC 70 or higher. Thus, when an object which is harder than the titanium based alloy material is held by such pliers, the underlying titanium based alloy material is likely to indent under the gripping force exerted by the jaws, and the titanium nitride coating crack. This occurs because the titanium based alloy is not sufficiently hard (i.e., strong enough) to support the thin coating, that is, the titanium nitride is not thick enough to be structurally self-supportive when coating the titanium based alloy.

The gripping faces of titanium based alloy pliers according to the present invention have a coating of hard and wear resistant material thereon of sufficient thickness to be structurally self-supportive under the forces exerted when an object which is harder than the underlying titanium based alloy material is being held by the plier jaws. Such coatings preferably are formable by a number of methods, including various spray coating processes. A flame spray coating process, described in greater detail hereinafter, has been used to successfully form such coatings. In general, flame spray coating processes utilize a combustible gas mixture, typically an oxygen-fuel gas, as a heat source to melt the coating material before it is sprayed in particle form onto a substrate. The coating materials used should exhibit good adhesion to titanium based alloys, with a surface texture having good gripping characteristics (e.g., a relatively high coefficient of friction). Good adhesion is generally dependent upon the compatibility of the coating material with the titanium based alloy and the spray coating process used. The surface texture is often dependant upon the size of the particles deposited. Larger particles tend to produce a rougher surface than smaller particles, often providing a gripping surface with a higher coefficient of friction and thus better gripping characteristics. If necessary, the coated particles are further treated by secondary heat processing to increase the density, and thereby the strength, of the layer of coating material. This secondary heat processing can also be used to increase the degree of adhesion (i.e., bonding) of the coating material to the underlying titanium based alloy material. However, this secondary heating can result in a smoother gripping surface and thus reduced gripping characteristics.

The preferred coating material is an alloy designated by the tradename Armacor M, in powder form. Armacor M is an alloy containing Fe, Cr, Si and B and manufactured by Amorphous Technologies International, Laguna Niguel, Calif. When flame spray coated, the Armacor M material typically has a hardness of about RC 65 and good adhesion to titanium based alloys. In addition, sprayed particles of the Armacor M material are large enough to form a coating having a surface texture (i.e., roughness) with good gripping characteristics. Because Armacor M resists oxidation, no secondary protective atmosphere is likely to be needed in the flame spray coating process. In addition, it is believed that the Armacor M coating can be as thin as about 50 microns and still be structurally self-supportive when backed by the gripping face of titanium based alloy pliers.

In the past, the gripping faces of orthodontic pliers made from hard stainless steel were usually knurled or serrated to improve their gripping characteristics. However, these serrations tended to scratch the orthodontic appliance being held. By using the Armacor M material, the present pliers made from titanium based alloys avoid this problem. Because of its good adhesion characteristics, the Armacor M material can be coated onto a relatively smooth surfaced gripping face. At the same time, while the Armacor M is hard and the surface of the coating is rough (i.e., has good gripping characteristics), it is not as rough and does not tend to scratch the appliance being held as readily, if at all, as prior stainless steel medical/dental pliers.

It is believed that for some types of pliers only one of the gripping faces would need to be coated. For example, bird beak pliers, such as those manufactured by the assignee of the present invention (Part No.'s 8030414 and 8030416), are likely to only need one gripping face coated, i.e., the curved face.

The present invention also comprehends medical/dental pliers made from titanium based alloys having a low friction, wear resistant coating on those areas of the pliers that are prone to wear. The particular areas of interest are the surfaces of the pivot joint which are in frictional contact with each other. By so coating these areas, the degree of wear previously exhibited can be significantly diminished and the functional life of the pliers extended. The plier halves are typically joined together at their pivot sections by a bolt or screw, also made of a titanium based alloy. The preferred way of reducing wear in the pivot joint of pliers made from titanium based alloys is to coat the surfaces of the pivot joint screw which are in frictional contact with either of the plier halves. It may also be necessary to coat the surfaces of the two pivot sections that are in frictional contact with each other.

The above and other objectives, features and advantages of the present invention will become apparent upon consideration of the following descriptions taken in conjunction with the accompanying drawings.

DETAILED DESCRIPTION OF THE INVENTION

Figure 1:
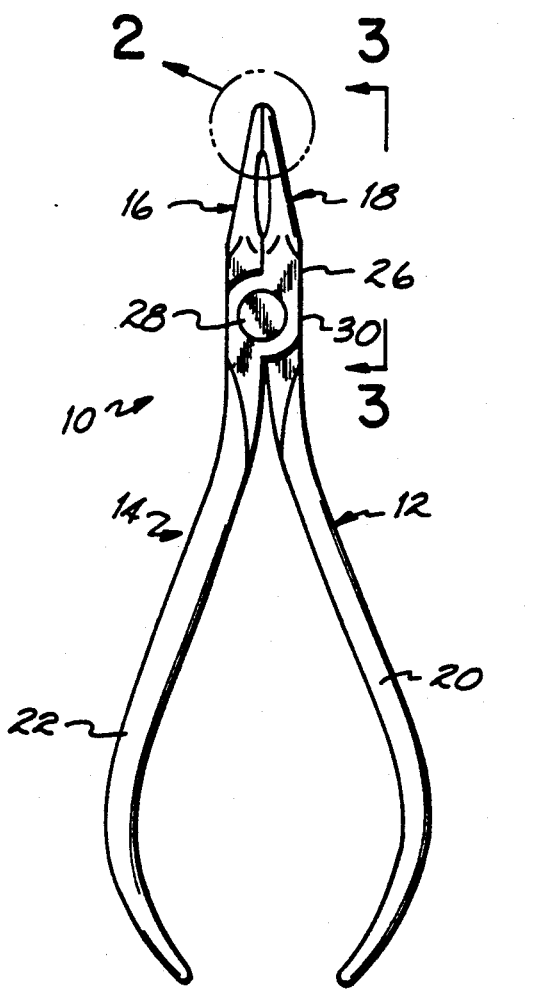
FIG. 1 is a top plan view of a pair of orthodontic pliers according to the present invention.
Figure 2:
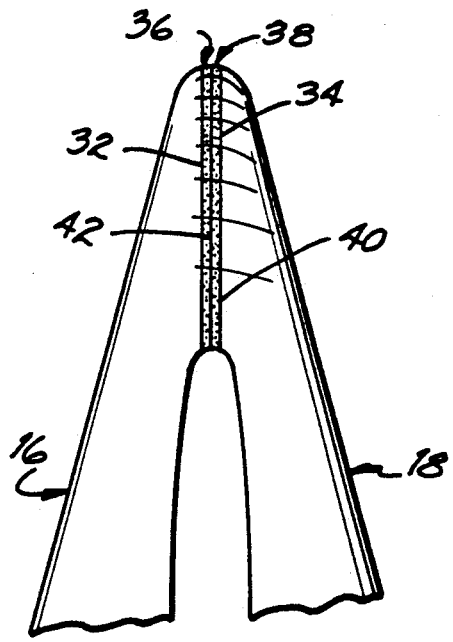
FIG. 2 is an enlarged view of the encircled area 2 of FIG. 1.
Figure 3:
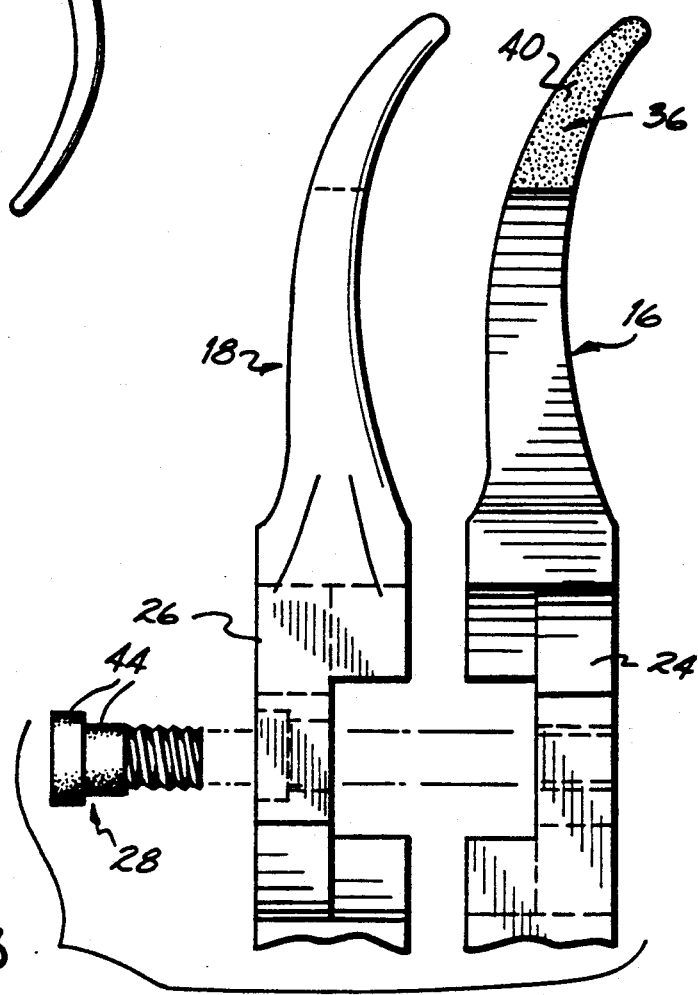
FIG. 3 is an exploded side elevational view of the pliers of FIG. 1 taken along lines 3—3.

While the present invention is applicable to medical/dental pliers in general, for the purpose of example, FIGS. 1-3 illustrate one embodiment of orthodontic pliers 10 made from a titanium based alloy according to the present invention. For some applications, the pliers 10 can be made from a titanium based alloy having a tensile strength of at least about 130,000 psi (i.e., about 897 MN/m$^2$). However, for most applications, the titanium based alloy should have a tensile strength of at least about 150,000 psi (i.e., about 1,035 MN/m$^2$). In addition, the preferred titanium alloy has a composition in weight percent of aluminum—6%, vanadium—4% and titanium—balance. The pliers 10 include two plier halves 12, 14, with each plier half having a jaw 16, 18 at one end, a handle 20, 22 at the other end, and a pivot section 24, 26 therebetween, respectively. The pivot sections 24, 26 receive each other in a nesting relation and are pivotally connected together, for example, by a screw 28 to form a pivot joint 30. Each of the jaws 16, 18 has a gripping face 32, 34. Each of the gripping faces 32, 34 has a coating 36, 38, respectively, of hard and wear resistant material deposited thereon. Each of the coatings 36, 38 has a surface 40, 42, respectively, for making gripping contact with an object such as an orthodontic appliance being held therebetween. Each of the coatings 36, 38 is of sufficient thickness to be structurally self-supportive against forces exerted thereon when an orthodontic appliance which is harder than the titanium based alloy material underlying the coatings 36, 38 is being held by the plier jaws 16, 18.

When the pivot sections 24, 26 are connected together by the joint screw 28, the pivot joint 30 allows pivotal movement between the plier halves 12, 14. Thus, the handles 20, 22 can be manipulated toward or away from each other to cause the jaws 16, 18 to open or close, respectively, and thereby the gripping surfaces 40, 42 to separate or move together in a gripping fashion.

To avoid excessive wear in the pivot joint area 30 and thereby increase the functional life of the pliers 10, a low friction, wear resistant coating material can be applied to the surfaces in the pivot joint 30 which are in frictional contact with each other. For the particular pliers 10 shown in the figures, a coating 44 of low friction, wear resistant material is preferably formed on the surfaces of the pivot joint screw 28 which would otherwise be in frictional contact with plier half 14. It may also be necessary to coat surfaces of the pivot sections 24, 26 of the plier halves 12, 14 that are in frictional contact with each other.

In a preferred embodiment of the present invention, the material used for coatings 36, 38 is a metallic alloy in powder form designated by the tradename Armacor M. Armacor M is manufactured by Amorphous Metals Technologies International, 27722 El Lazo, Laguna Niguel, Calif., 92656, and has the following general composition by weight percent:

chromium—50% max.
silicon—3% max.
boron—8% max.
iron—balance.

In addition, Armacor M has a melting point of approximately 2,200° F. (1204° C.) and a specific gravity of approximately 7.4 (water equalling 1).

The coatings 36, 38 are formed by spray coating the Armacor M particles onto the gripping faces 32, 34 of the plier jaws 16, 18 until a structurally self-supportive layer of the material is deposited. It is believed that an Armacor M coating thickness of at least about 50 microns should be sufficient. Satisfactory results have been obtained using thicknesses within the range of about 250 microns to about 1000 microns. However, a thickness of about 500 microns is preferred. While various spray coating processes can be used to deposit the Armacor M and other suitable coating materials onto the gripping faces 32, 34 of the pliers 10, optimum results have been obtained when a flame spray coating process was used. In general, flame spray coating processes utilize a combustible gas, typically an oxygen-fuel gas mixture, as a heat source to melt the coating material before it is sprayed in particle form onto a substrate. Flame spray coating equipment is available for use with coating materials which are originally in either rod, wire, or power form. However, powdered Armacor M is preferred. Armacor M is a self-fluxing, hard facing powder. Its resistance to oxidation enables it to be used in flame spray coating processes without the need for a protective atmosphere. In addition, when flame spray coated, the Armacor M material has good adhesion to titanium based alloys and has a hardness of at least about RC 55 and preferably about RC 65.

The preferred flame spray coating process utilized is generally described as the Diamond Jet System manufactured by Metco, a division of Perkin-Elmer, Inc., Westbury, N.Y. Coatings produced with the Diamond Jet System develop very high densities. Densities of greater than 95% of theoretical density can be obtained, and in most cases, densities of 98-99% have been obtained. These high densities help to increase the bond strength and hardness of the coating. Relatively high coating thicknesses can be obtained with the Diamond Jet System. Particular pieces of Diamond Jet System equipment which have been employed to form coatings of Armacor M according to this invention are described as follows:

Spray gun—Model No. DJA
Fluid control unit—Model No. DJC
Powder feed unit—Model No. DJP An example of pertinent process parameters used with this equipment when forming coatings according to this invention is as follows:

1. Powder type: Armacor "M", +325 −400 mesh.
2. Equipment control settings:
    Power rate: 4.5 to 5.0 lbs/hour
    Fuel: 39-40%
    Nitrogen flow: 55
    Oxygen ratio: 45-46%
    Air pressure: 49-50 psi
3. Operator parameters, with six adjacent gripping surfaces in a row:
    Total cycle time: one pass over all six gripping faces in about 1 second
    Nozzle distance: about 12" from each gripping face
    Total number of passes: approximately 60

Note: Gripping faces should be sandblasted before coating, and no time delay is necessary between passes.

In general, the particle size of the coating material being deposited can influence the texture of the gripping surfaces 40, 42 of the coatings 36, 38, with larger particles tending to produce a rougher surface texture than smaller particles. A rougher surface texture often results in better gripping characteristics due to a higher coefficient of friction. Armacor M coatings 36, 38 having gripping surfaces 40, 42 with sufficiently rough surface textures have been obtained using Armacor M with the powder having a mesh size of as small as −400 (i.e., particles of about 37 microns or smaller). Powder having a mesh size ranging from about −270 to about +325 is preferred. However, larger particles should also work sufficiently. As discussed previously, indications are that the rough surface textures obtained with Armacor M will not detrimentally scratch or mar the orthodontic appliance being held like prior stainless steel pliers (not shown) which had knurled or serrated gripping faces.

While Armacor M is the preferred coating material, tungsten carbide appears to be a suitable coating material, also. Coatings of tungsten carbide are not as adherent to titanium based alloys as Armacor M and the typical size of the particles deposited is usually much smaller than particles of the Armacor M material. Therefore, it is expected that in order to use tungsten carbide as a coating material on medical/dental pliers made from a titanium based alloy, the gripping faces 32, 34 of the plier jaws 16, 18 will have to be pretextured or roughened before the coating material is applied in order to assure adequate adherence to the gripping faces 32, 34, and that the resulting gripping surfaces 40, 42 have good gripping characteristics, such as a sufficiently high coefficient of friction to enable an orthodontic appliance to be securely gripped between the jaws 16, 18.

As previously discussed, to increase the functional life of the pliers 10, a low friction, wear resistant coating material can be applied to the surfaces in the pivot joint 30 which are in frictional contact with each other. By so coating these areas, the degree of wear previously exhibited by such pliers 10 can be significantly diminished. While it may be necessary to coat surfaces of the pivot sections 24, 26 of the plier halves 12, 14 that are in frictional contact with each, satisfactory results have been obtained by only applying coatings 44 to the pivot joint screw 28. While it is preferable to use Armacor M and other comparable Armacor alloys to coat the frictional contact surfaces of the pivot joint screw 28, other materials can also be used. For example, a Vespel polymer or teflon material. A tiodize, titanium nitride, or titanium carbide coating could also be used.

From the above disclosure of the general principles of the present invention and the preceding detailed description, those skilled in the art will readily appreciate the various changes and modifications to which the present invention is susceptible. Therefore, the scope of the present invention should be limited only by the following claims and equivalents thereof.

What is claimed is:

1. Pliers for gripping objects comprising:
   a pair of plier halves made from a titanium based alloy material, each of said plier halves having a handle, a jaw and a pivot section, each of said jaws having a gripping face;
   connecting means for connecting the pivot sections of said pair of plier halves to form a pivot joint such that said handles can be manipulated to cause said gripping faces of jaws to move together in a gripping fashion; and
   a coating of hard and wear resistant material on at least one of said gripping faces, said coating being of sufficient thickness to be structurally self-supportive against forces exerted thereon when an object which is harder than the titanium based alloy material underlying said coating is being held by said plier jaws.

2. The pliers of claim 1 wherein said coating is at least about 50 microns thick.

3. The pliers of claim 2 wherein the thickness of said coating is in the range of about 250 to 1,000 microns.

4. The pliers of claim 1 wherein said coating is formed from a plurality of particles of said hard and wear resistant material.

5. The pliers of claim 1 wherein said hard and wear resistant material is Armacor M.

6. The pliers of claim 1 wherein said hard and wear resistant material is tungsten carbide.

7. The pliers of claim 1 wherein said coating has a hardness of at least about RC 55.

8. The pliers of claim 7 wherein said coating has a hardness of about RC 65.

9. The pliers of claim 1 wherein each of said gripping faces is pretextured before said coating is applied.

10. The pliers of claim 1 wherein said titanium based alloy material has a tensile strength of at least about 130,000 psi.

11. The pliers of claim 1 wherein said pivot joint has surfaces in frictional contact which are coated with a low friction, wear resistant material.

12. The pliers of claim 11 wherein said connecting means includes a pivot joint screw having wear surfaces in frictional contact with either of said plier halves, the wear surfaces of said pivot joint screw being coated with a low friction, wear resistant material.

* * * * *